United States Patent
Feher

(10) Patent No.: US 7,827,620 B2
(45) Date of Patent: *Nov. 9, 2010

(54) AIR CONDITIONED HELMET APPARATUS

(76) Inventor: Steve Feher, 1 Keahole Pl., #1505, Honolulu, HI (US) 95825

(\*) Notice: Subject to any disclaimer, the term of this patent is extended or adjusted under 35 U.S.C. 154(b) by 0 days.

This patent is subject to a terminal disclaimer.

(21) Appl. No.: 11/252,089

(22) Filed: Oct. 17, 2005

(65) Prior Publication Data

US 2006/0053529 A1    Mar. 16, 2006

Related U.S. Application Data

(63) Continuation of application No. 10/601,964, filed on Jun. 23, 2003, now Pat. No. 6,954,944.

(51) Int. Cl.
   *A42C 5/04* (2006.01)
(52) U.S. Cl. .............. 2/171.3; 2/410; 2/411; 2/425; 128/201.24
(58) Field of Classification Search ............ 2/171.3, 2/424, 436, 437, 6.1, 6.2, 6.3, 411, 412, 414, 2/906, 7, DIG. 1; 454/370; 607/109–110; 165/46; 62/259.3; 128/201.22, 200.28, 201.24, 128/201.25, 205.29, 201.15
See application file for complete search history.

(56) References Cited

U.S. PATENT DOCUMENTS

| | | | | |
|---|---|---|---|---|
| 2,222,635 | A * | 11/1940 | Smith ................ | 128/201.25 |
| 2,826,758 | A | 12/1955 | Kahn | |
| 3,223,086 | A | 12/1965 | Denton | |
| 3,293,659 | A * | 12/1966 | Shepard ............. | 128/201.15 |
| 3,713,480 | A | 1/1973 | Low et al. | |
| 3,911,914 | A * | 10/1975 | Johansson .......... | 128/201.23 |
| 3,963,021 | A | 6/1976 | Bancroft | |
| 4,054,953 | A * | 10/1977 | De Barsy ............ | 2/414 |
| 4,172,495 | A * | 10/1979 | Zebuhr et al. ....... | 165/46 |
| 4,280,491 | A * | 7/1981 | Berg et al. .......... | 128/201.24 |
| 4,475,248 | A * | 10/1984 | L'Abbe et al. ...... | 2/2.5 |
| 4,483,021 | A * | 11/1984 | McCall .............. | 2/7 |

(Continued)

FOREIGN PATENT DOCUMENTS

GB        2014036        8/1979

(Continued)

OTHER PUBLICATIONS

PCT/IB2004/01524 International Search Report (Dated Feb. 22, 2005).

(Continued)

*Primary Examiner*—Shaun R Hurley
*Assistant Examiner*—Andrew W Sutton
(74) *Attorney, Agent, or Firm*—Robert J. Lauson; Lauson & Tarver, LLP

(57) ABSTRACT

A helmet (12) includes a thermoelectric heat pump (14) mounted onto a rear surface of the helmet shell (12) for delivering temperature conditioned air to the interior of the helmet shell. A multi-layer structure (48) on the helmet shell interior distributes conditioned air across the scalp and directly onto the face. An optional scoop (38) directs ambient air to the heat pump (14). Another version locates the heat pump (68, 84) remotely and conditioned air is transmitted to the helmet apparatus (70, 78) via a flexible conduit (72, 85).

19 Claims, 4 Drawing Sheets

U.S. PATENT DOCUMENTS

| | | | | |
|---|---|---|---|---|
| 4,502,480 | A * | 3/1985 | Yamamoto | 128/201.15 |
| 4,549,541 | A * | 10/1985 | Sundahl | 128/201.19 |
| 4,586,200 | A * | 5/1986 | Poon | 2/413 |
| H902 | H * | 4/1991 | Rousseau | |
| 5,014,363 | A * | 5/1991 | Hubner et al. | 2/243.1 |
| 5,050,240 | A * | 9/1991 | Sayre | 2/6.2 |
| 5,054,479 | A * | 10/1991 | Yelland et al. | 128/201.25 |
| 5,146,757 | A * | 9/1992 | Dearing | 62/61 |
| 5,197,294 | A | 3/1993 | Galvan et al. | |
| 5,283,914 | A * | 2/1994 | James | 2/424 |
| 5,533,500 | A * | 7/1996 | Her-Mou | 128/201.25 |
| 5,603,728 | A * | 2/1997 | Pachys | 607/110 |
| 5,921,467 | A | 7/1999 | Larson | |
| 6,081,929 | A | 7/2000 | Rothrock et al. | |
| 6,085,369 | A * | 7/2000 | Feher | 5/423 |
| 6,954,944 | B2 * | 10/2005 | Feher | 2/171.3 |
| 2004/0255364 | A1 * | 12/2004 | Feher | 2/171.3 |

FOREIGN PATENT DOCUMENTS

GB 2274238 A * 7/1994

OTHER PUBLICATIONS

EP2004730895 Office Action (Dated Feb. 15, 2007).

Feher; 931111, Thermoelectric Air Condo Variable Temperature Seat (VTS)...; Copyright 1998 Society of Automotive Engineers, Inc. pp. 341-349.

Feher; 980661, Stirling Air Cond. Variable Temperature Seat, (SVTS)...; Copyright 1998 Society of Automotive Engineers, Inc. pp. 1-9.

* cited by examiner

AIR CONDITIONED HELMET APPARATUS

CROSS-REFERENCE TO RELATED APPLICATION

This application is a continuation of U.S. application Ser. No. 10/601,964 filed Jun. 23, 2003, now U.S. Pat. No. 6,954,944.

BACKGROUND

1. Field of the Invention

The present invention relates to a helmet apparatus especially adaptable for providing conditioned air about the head and face of the wearer, and which is light-weight and only requires relatively low-power electrical energization.

2. Description of Related Art

There are many situations, both work oriented and sport, in which the wearing of a helmet is necessary or highly desirable. Exemplary of but a few instances where wearing a helmet for a relatively long period of time is required are: a motorcycle police officer; race car driver; and a military tank driver. Considerable discomfort can result from wearing a helmet, especially the full-face type, for even a short period of time particularly in warm or humid weather.

SUMMARY OF INVENTION

In the practice of a first embodiment of the invention there is provided a helmet consisting of the hard shell variety onto the rear of which is mounted an electrically energized heat pump that produces a temperature conditioned air stream for moving along a conduit past the rear wall of the helmet, through a special liner of the helmet adjacent the top of the head of the wearer, and finally directly contacting the forehead and face. For cooling the air, the heat pump is preferably a thermoelectric device (e.g., Peltier) or, alternatively, a Stirling cycle device. A detachable electric cable interconnects with the heat pump and extends downwardly and away from the wearer's body for lower end interconnection with a suitable power supply (e.g., battery of a motorcycle or automotive vehicle).

Optionally, a forwardly facing air scoop is mounted to the outside upper surface of the helmet and directs ambient air to the heat pump for conditioning while also serving to protect the heat pump from possible impact or contact damage. As a further option, an air filter of either the depth variety or carbon absorption type can be utilized to remove foreign particles (e.g., dirt, dust, pollen) and noxious fumes from inlet air before it is processed by the heat pump.

In yet another embodiment, the helmet is constructed generally as in the first embodiment, but the heat pump is conveniently located adjacent to and separated from the helmet. The conditioned air is communicated from the heat pump to the helmet via a flexible tubular conduit.

BRIEF DESCRIPTION OF THE DRAWING

These and other objects of the present invention will become more readily apparent upon reading the following detailed description and upon reference to the attached drawings.

DESCRIPTION OF PREFERRED EMBODIMENTS

There are a number of different human activities that require or where it is highly desirable to wear, a helmet to protect the wearer against injury while engaging in the activity. For example, a helmet is desirably worn when riding a motorcycle or driving a race car since any accident could result in a blow being received to the head and if a helmet is worn the chances of reducing or avoiding injury altogether are substantially increased. On wearing a helmet while riding a motorcycle or during car racing, the driver is subjected to increased temperature about the head especially during warm weather or humid conditions which are rather uncomfortable for the driver/wearer. A motorcycle policeman, for example, must wear a helmet throughout long hours of a work shift and suffer the inconvenience associated therewith along with the normal high stress related to his employment.

Figure 1:
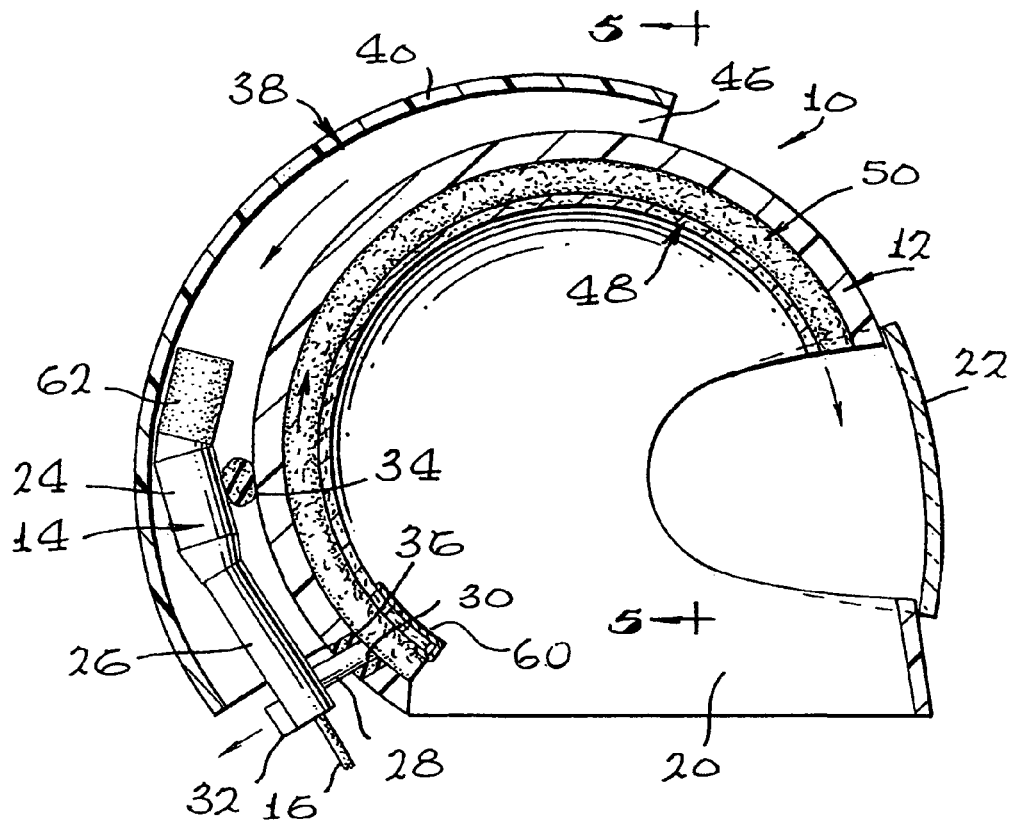
FIG. 1 is a side elevational, partially sectional view of a helmet with air conditioning apparatus of this invention mounted thereon.

With reference now to the drawing and particularly to FIG. 1, a first embodiment of air conditioned helmet apparatus of the present invention is enumerated generally as 10 and includes in its major parts a helmet 12 of the rigid variety, an air conditioning apparatus 14 secured to an outer rear surface of the helmet, and an electric cable 16 for removable connection to a conveniently adjacent power source.

The helmet 12 preferably has a rigid and rugged outer shell which is substantially imperforate other than having specific openings for purposes to be described and an open bottom 20 via which the helmet is received onto the head of a wearer (not shown). More particularly, the helmet shell 12 can be cast from a tough relatively lightweight plastic or metal and includes a transparent, adjustably movable visor 22 affixed in what is a forward wall of the helmet shell.

The air conditioning apparatus 14 is secured to the rear of the helmet and includes a blower mechanism 24 which delivers pressurized ambient air to a heat pump 26 where part of the air stream is moved across a "cold" part (when cooling is desired) to a conduit 28 and passed through a notch or opening 30 in the helmet back lower edge for distribution to the helmet interior as will be described. A further part of the air stream from the blower mechanism passes simultaneously over the apparatus "hot" part and moves outwardly through the conduit 32 removing waste heat to the ambient. A compliant support 34 (e.g., rubber, Sorbothane) cooperating with a rubber or Sorbothane seal 36 serves to mechanically secure the apparatus 14 to the helmet while maintaining noise and vibration at a low level.

Still referring to FIG. 1, an optional air scoop 38 includes a curved elongated central wall 40 extending from approximately the top center outer surface of the helmet shell to a point opposite the lower part of the shell facing the back of a helmet wearer's neck, which wall 40 is mounted to the helmet shell by first and second sidewalls 42 and 44. By this construction, on movement of the associated vehicle (e.g., motorcycle), the scoop 38 receives external air from the ambient via an opening 46 that passes along the scoop interior spacing (arrows) from the helmet shell outer surface to be acted upon by the air conditioning apparatus 14.

Figure 4:
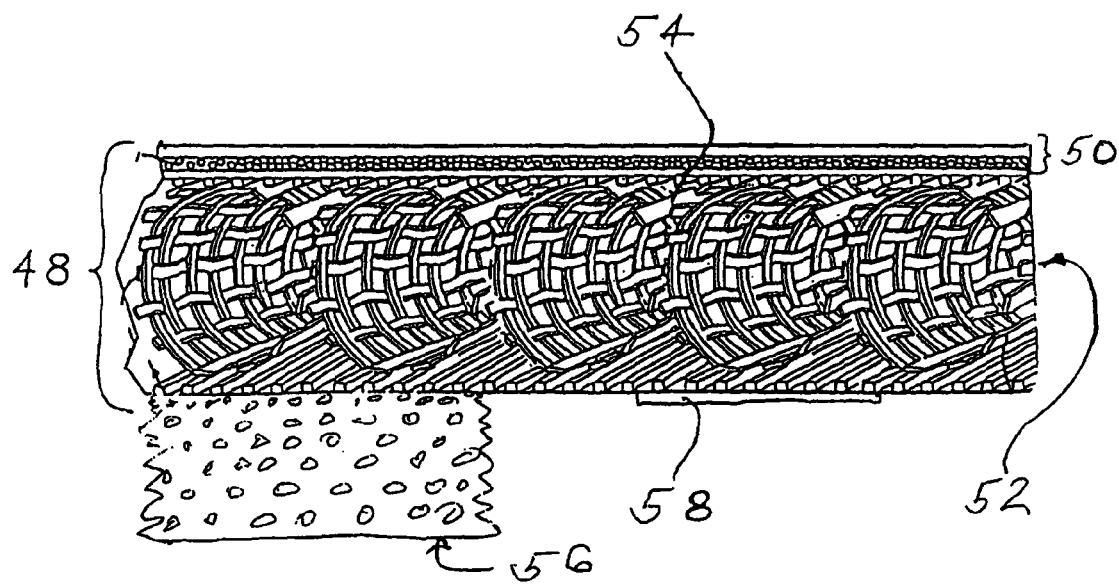
FIG. 4 is an enlarged sectional view taken through the multi-layer structure lining the helmet.
Figure 5:
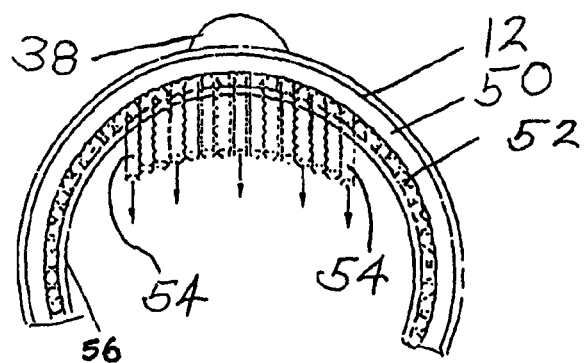
FIG. 5 is a front elevational sectional view of the helmet apparatus taken along the line 5-5 of FIG. 1.

With simultaneous reference to FIGS. 1 and 4, the inside of the helmet shell 12 is covered with a multi-layer structure 48 which serves to both protect the wearer's head, conduct conditioned air along a path adjacent the helmet shell interior, and finally release the conditioned air to move past face of the wearer (arrows). More particularly, the structure 48 includes a first layer 50 covering and contacting the inner surface of the helmet shell 12 that is constructed of an impact absorbing material having a primary function of protecting a wearer's head against impact shock. Onto the impact absorbing layer, there is laid down a second or air-conduiting layer 52 preferably formed from a tubular textile material 54 which readily conducts air along the major axis of the tubular material and to a lesser extent transversely through the walls of the material. The tubular material includes woven tubes interwoven with each other which do not compress more than 5 percent during wearing use of the helmet shell. The tubular material extends from approximately the lower rear edge of the helmet to terminate just in front a wearer's forehead (FIG. 5). Accordingly, the conditioned air effects heat transfer to the head primarily by convection and moves directly across the face as shown by the arrows.

Optionally, a third layer 56 laid down on the inwardly facing surface of the second layer 52 is constructed of an open-cell cushion foam that is comfortable to the touch. Alternatively, an extent of cloth 58 covers the foam layer, or can substitute for the foam layer, and is colored a dark color (e.g., black) to reduce giving a soiled appearance.

A band or ribbon 60 of insulation material is wrapped around the lower rear edge of the multi-layer structure 48 and extending for about one-half of the helmet periphery (FIG. 1). The ribbon is sealed about the structure 48 (e.g., by adhesive) to insure a more uniform passage of conditioned air along the textile tubular layer 52 and finally directed onto the face of a wearer. Also, the ribbon provides insulation against excessive temperature change being induced in the wearer's neck region from the conditioned air.

A filter 62 can be optionally located at the air inlet of the pump apparatus 14 for removing foreign particles, such as dirt, dust and pollen, for example or noxious fumes, that are carried by the ambient air.

As to general operation of the versions described, pressurized conditioned air moves from the apparatus 14 through the helmet notch or opening 30, along the tubes of the second layer 52, downwardly onto the wearer's forehead, face and temples, and finally exiting at the lower front of the helmet to the ambient air. This movement of conditioned air downwardly across the face not only refreshes the wearer by contact and provides fresh air for breathing, but also reduces the production of fog on the visor and thus maintains clear visibility.

Figure 2:
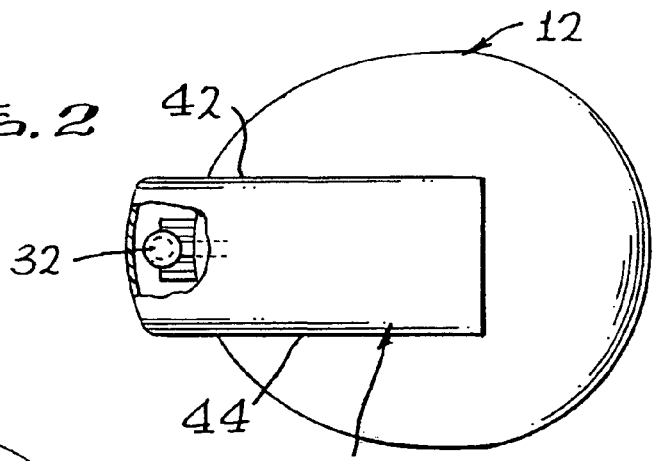
FIG. 2 is a top plan, partially sectional view of the helmet apparatus of FIG. 1 shown with a single blower device.

Although there are other devices that can be utilized to cool an air stream for present purposes, because of use context (e.g., a motorcycle) it is important that the device take as little electrical power as possible and since the cooling apparatus in a first embodiment is carried on a helmet the apparatus weight must be minimal. In a practical construction of the invention using a single blower mechanism (FIGS. 1 and 2) and a Peltier thermoelectric cooling apparatus, the entire weight of the apparatus 14 did not exceed about 0.5 pounds.

Figure 6:
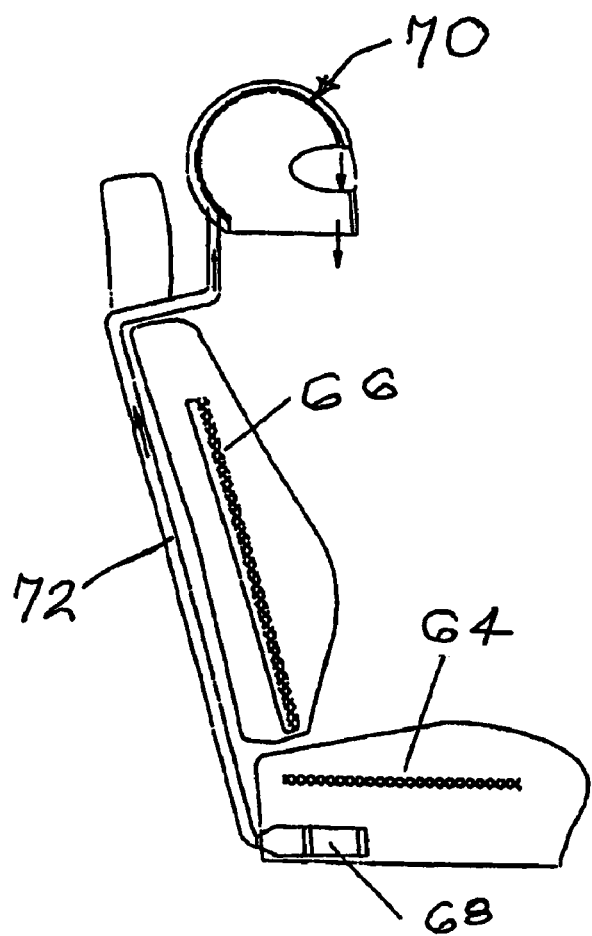
FIG. 6 is an elevational view of yet another embodiment where the heat pump is separately mounted from the helmet.

For a further embodiment of the invention that is especially adapted to for use in an automotive vehicle (e.g., race car), reference is now made to FIG. 6. A typical automotive vehicle seat 64 and associated backrest 66 are shown with a heat pump 68 (which can be identical to the heat pump 14) that is conveniently mounted to the seat 64. Helmet apparatus 70, which can be identical to the previously described apparatus 10 with the apparatus 14 removed, is interconnected with the heat pump 68 by an appropriate length of flexible tubing 72 that preferably extends up the back of the backrest 66 (FIG. 3).

Figure 3:
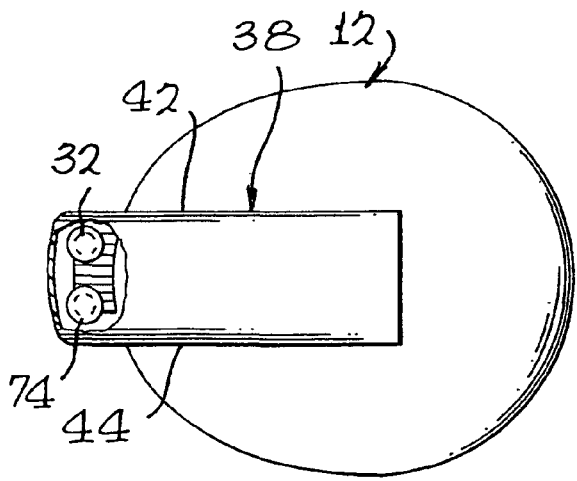
FIG. 3 is a further top plan, partially sectional view of the helmet apparatus of FIG. 1 with a double blower device.

Efficiency improvement of the heat pump in any of the described embodiments and options can be achieved by adding a separate or second blower mechanism 74 solely used to empty waste heat from the apparatus 14 to the ambient (FIG. 3).

Figure 7:
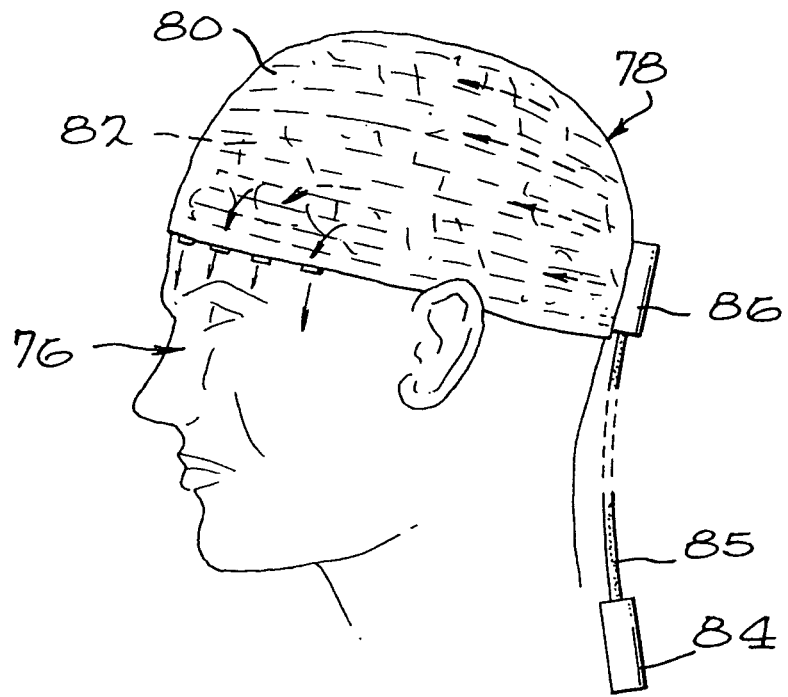
FIG. 7 is an elevational partially sectional view of a still further version of the invention as applied to a patient.

Turning now to FIG. 7, there is shown a version of the invention especially advantageous for wear by a patient 76 in need of having the head maintained at a prescribed temperature. In particular, an air-conditioned helmetlike headgear 78 consists of a close fitting textile, flexible rubber or molded plastic cap 80 which is dimensioned for secure fitting to the patient's head. A layer 82 of textile tubular means which can be identical to the previously described layer 52 is secured to the interior surface of the cap 80 with the individual tubes extending from the back lower edge to a termination point at the forehead of the patient. A conveniently mounted heat pump 84 (either thermoelectric or Stirling cycle) provides conditioned air via a flexible conduit 85 and a fitting 86 at the back of the cap to the layer 82 such that conditioned air moves along the textile tubes adjacent the scalp and exits at the forehead downwardly onto the face of the patient.

Figure 8:
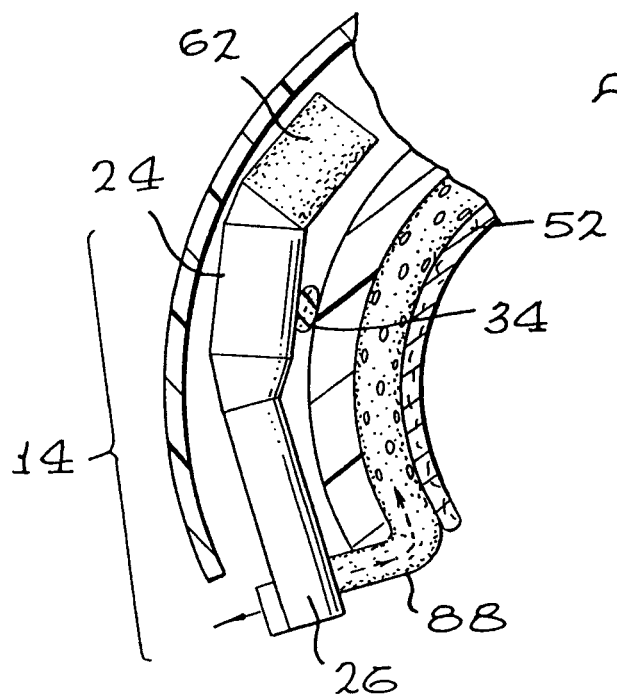
FIG. 8 is an enlarged detail view of an alternative version of a conditioned air conduit connection with a multi-layer structure.

An alternative manner of transferring conditioned air from the apparatus 14 to the conduiting layer 52 is shown in FIG. 8. More particularly, a tubular conduit 88 has one end in air receiving connection with the heat pump 26 and after extending around and past the rear lower edge of the helmet shell 12 has its other end in contact with the layer 52. By this construction, a further or second opening does not have to be formed in the helmet shell.

Although the invention has been described in connection with preferred embodiments, it is to be understood that those skilled in the appertaining arts may contemplate modifications within the spirit of the invention as described and shown herein and within the ambit of the appended claims.

What is claimed is:

1. A helmet apparatus, comprising:
   a rigid helmet shell including a first opening of such dimensions as to permit receipt onto the head of a wearer;
   multi-layer means secured to an interior surface of the helmet shell constructed of materials enabling air to readily pass therealong and empty directly onto the face of a wearer; and
   a device for producing a pressurized stream of air in fluid communication with the multi-layer means;
   in which the multi-layer means includes a first layer of an impact resistant material adhered to a helmet shell interior surface, and a second layer contacting the first layer constructed of an air permeable textile material having a plurality of longitudinally extended tubular structures to guide the air passing readily therealong in a direction generally from back to front of the helmet shell, a portion of the air permeating transversely through the textile material onto a scalp of the wearer.

2. The helmet apparatus as in claim 1, in which a third layer constructed of an open-cell foam is provided secured onto an outer surface of the second layer.

3. The helmet apparatus as in claim 1, in which the device is a heat pump.

4. The helmet apparatus as in claim 1, in which cabling has one end connected to the device and extends downwardly along a gravity path for connection at its other end to a suitable source of power.

5. The helmet apparatus as in claim 1, in which the tubular textile material includes woven tubes interwoven with each other which do not compress more than five percent during wearing use of the helmet shell.

6. The helmet apparatus as in claim 1, in which the helmet apparatus is adaptable for wearing while driving a motorcycle at which time the cabling other end is interconnected with an electric energy source carried by the motorcycle.

7. The helmet apparatus as in claim 1, in which the device has an air inlet end and an air filter interrelates the air inlet end with ambient air.

8. The helmet apparatus as in claim 1, in which the device is mounted to an outside surface of the helmet shell.

9. The helmet apparatus as in claim 8, in which there is further provided an air scoop secured to an outer surface of the helmet shell protectively covering the device and for receiving air and directing it to the device.

10. The helmet apparatus as in claim 9, in which the scoop has a central wall and two sidewalls integral with the central wall and forming two open ends, the sidewalls being secured to the outer surface of the helmet shell so that the open ends are located in respective front and back relative positions.

11. The helmet apparatus as in claim 9, in which the device is affixed to the helmet shell via compliant means.

12. The helmet apparatus as in claim 1, in which the device is located remote from the helmet.

13. The helmet apparatus as in claim 1, in which an elongated sealing means is secured about the multi-layer structure adjacent the lower rear edge of the helmet shell preventing conditioned air escaping from the structure lower rear edge.

14. The helmet apparatus as in claim 3, in which the heat pump includes a single blower mechanism moving a first part of pressurized air over the "cold" place of the pump to the helmet shell interior when cooling is a conditioning mode of the device, and simultaneously moving a second part of the pressurized air past the "hot" place of the pump to the exterior ambient.

15. The helmet apparatus as in claim 8, in which the device includes two blower mechanisms, a first mechanism for moving conditioned air to the helmet interior and a second mechanism for moving waste heat or waste cooling, as the case may be, to the ambient exterior of the helmet shell.

16. A helmet apparatus, comprising:
   a helmet shell including a first opening of such dimensions as to permit receipt onto the head of a wearer;
   an air conduiting layer distributed about substantially the entire interior surface of the helmet shell, the air conduiting layer having an air permeable wall structure constructed of materials having a plurality of longitudinally extended tubular structures to guide the air to readily pass therealong and empty directly onto the face of a wearer and to a lesser extent pass by convection through the air permeable wall of the air conduiting layer onto the scalp of the wearer; and
   device for producing a pressurized stream of air in fluid communication with the air conduiting layer.

17. The helmet apparatus of claim 16 wherein the air conduiting layer is constructed of a tubular textile material.

18. A helmet apparatus, comprising:
   a helmet shell including a first opening of such dimensions as to permit receipt onto the head of a wearer;
   a device for producing a pressurized stream of air; and
   a plenum distributed about substantially the entire interior surface of the helmet shell and in fluid communication with the device, the plenum having an air permeable surface proximate the wearer's scalp and a vent proximate the wearer's forehead, wherein the air permeable surface defines a plurality of longitudinally extended tubular structures to guide the pressurized stream of air to primarily flows along inside the plenum and vents across the wearer's face, a portion of the pressurized stream escaping transversely through the air permeable surface of the plenum onto the wearer's scalp.

19. The helmet apparatus of claim 18 wherein the plenum comprises a plurality of tubular conduits.

\* \* \* \* \*